US00PP15357P2

(12) United States Plant Patent
Oliver

(10) Patent No.: US PP15,357 P2
(45) Date of Patent: Nov. 23, 2004

(54) ***HEUCHERA* PLANT NAMED 'SHENANDOAH MOUNTAIN'**

(50) Latin Name: *Heuchera×hybrida*
Varietal Denomination: Shenandoah Mountain

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/775,952

(22) Filed: Feb. 10, 2004

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Heuchera* plant named 'Shenandoah Mountain', characterized by its full, densely foliated and uniformly mounded plant habit; relatively large and vigorous plant habit; bronze and silver-colored foliage; numerous showy white-colored flowers arranged on erect panicles; and excellent garden performance.

2 Drawing Sheets

Botanical classification/cultivar designation: *Heuchera×hybrida* cultivar Shenandoah Mountain.

BACKGROUND OF THE INVENTION

The present invention relates to a new and distinct cultivar of *Heuchera* plant, botanically known as *Heuchera×hybrida* and hereinafter referred to by the name 'Shenandoah Mountain'.

The new *Heuchera* is a product of a planned breeding program conducted by the Inventor in Scottdale, Pa. The objective of the breeding program is to create new *Heuchera* cultivars having good plant vigor, dense and uniform plant habit, and showy and attractive flower and leaf coloration.

The new *Heuchera* was discovered by the Inventor in a controlled environment in Scottdale, Pa., from seedling progeny from a cross-pollination made by the Inventor in May, 1999, of the *Heuchera×hybrida* cultivar Silver Scrolls, disclosed in U.S. Plant Pat. No. 12,066, as the female, or seed, parent with an unidentified selection of *Heuchera alba*, not patented, as the male, or pollen, parent. The new *Heuchera* was selected by the Inventor in July, 2001. The selection of this plant was based on its desirable flower and foliage coloration.

Asexual reproduction of the new *Heuchera* by cuttings in a controlled environment in Scottdale, Pa., since October, 2001, has shown that the unique features of this new *Heuchera* are stable and reproduced true to type in successive generations.

SUMMARY OF THE INVENTION

The cultivar Shenandoah Mountain has not been observed under all possible environmental conditions. The phenotype may vary somewhat with variations in environment such as temperature and light intensity, without, however, any variance in genotype.

The following traits have been repeatedly observed and are determined to be the unique characteristics of 'Shenandoah Mountain'. These characteristics in combination distinguish 'Shenandoah Mountain' as a new and distinct cultivar of *Heuchera:*

1. Full, densely foliated and uniformly mounded plant habit.
2. Relatively large and vigorous plant habit.
3. Bronze and silver-colored foliage.
4. Numerous showy white-colored flowers arranged on erect panicles.
5. Excellent garden performance.

Plants of the new *Heuchera* can be compared to plants of the female parent, the cultivar Silver Scrolls. In side-by-side comparisons conducted by the Inventor in Scottdale, Pa., plants of the new *Heuchera* differed from plants of the cultivar Silver Scrolls in the following characteristics:

1. Plants of the new *Heuchera* were large and had larger leaves than plants of the cultivar Silver Scrolls.
2. Plants of the new *Heuchera* and the cultivar Silver Scrolls differed in leaf and flower coloration.

Plants of the new *Heuchera* can be compared to plants of the male parent selection. In side-by-side comparisons conducted by the Inventor in Scottdale, Pa., plants of the new *Heuchera* differed from plants of the male parent selection in the following characteristics:

1. Plants of the new *Heuchera* were larger with longer peduncles than plants of the male parent selection.
2. Plants of the new *Heuchera* and the male parent selection differed in foliage shape and coloration.
3. Plants of the new *Heuchera* had smaller flowers than plants of the male parent selection.

Plants of the new *Heuchera* can be compared to plants of the cultivar Regina, not patented. In side-by-side comparisons conducted by the Inventor in Scottdale, Pa., plants of the new *Heuchera* differed from plants of the cultivar Regina in the following characteristics:

1. Plants of the new *Heuchera* were larger than plants of the cultivar Regina.
2. Plants of the new *Heuchera* had smaller leaves than plants of the cultivar Regina.
3. Plants of the new *Heuchera* and the cultivar Regina differed in leaf and flower coloration.
4. Plants of the new *Heuchera* had tighter and less spreading inflorescences than plants of the cultivar Regina.

Plants of the new *Heuchera* can also be compared to plants of the cultivar Silver Lode, disclosed in U.S. Plant Pat. No. 13,339. In side-by-side comparisons conducted by the Inventor in Scottdale, Pa., plants of the new *Heuchera* differed from plants of the cultivar Silver Lode in the following characteristics:

1. Plants of the new *Heuchera* and the cultivar Silver Lode differed in leaf coloration.
2. Plants of the new *Heuchera* had shorter inflorescences than plants of the cultivar Silver Lode.
3. Plants of the new *Heuchera* had larger flowers than plants of the cultivar Silver Lode.

BRIEF DESCRIPTION OF THE PHOTOGRAPHS

The accompanying colored photographs illustrate the overall appearance of the new *Heuchera*, showing the colors as true as it is reasonably possible to obtain in colored reproductions of this type. Colors in the photographs may differ slightly from the color values cited in the detailed botanical description which accurately describe the colors of the new *Heuchera*.

The photograph on the first sheet comprises a side perspective view of a typical one-year old flowering plant of 'Shenandoah Mountain'.

The photograph on the second sheet is a close-up view of a typical inflorescence of 'Shenandoah Mountain'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following detailed botanical description describe plants grown in Scottdale, Pa. during the summer in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C.

Botanical classification: *Heuchera×hybrida* cultivar Shenandoah Mountain.

Parentage:

*Female, or seed, parent.*—*Heuchera×hybrida* cultivar Silver Scrolls, disclosed in U.S. Plant Pat. No. 12,066.

*Male, or pollen, parent.*—Unidentified selection of *Heuchera alba*, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded and uniform plant habit with upright panicles with white-colored flowers. Vigorous growth habit; relatively large plants.

*Plant size.*—Height, soil level to top of foliar plane: About 25 cm. Height, soil level to top of panicles: About 75 cm. Diameter or spread: About 50 cm.

*Foliage description.*—Arrangement: Basal rosette, simple. Length: About 9 cm. Width: About 8 cm. Shape: Rounded cordate; seven-lobed. Apex: Broadly obtuse, lobed. Base: Cordate. Margin: Crenate with fine ciliation. Texture, upper and lower surfaces: Slightly rough and slightly pubescent. Venation pattern: Palmate, reticulate. Color: Developing and fully expanded leaves, upper surface: 183C underlain with 200A and mottled with 198D. Developing and fully expanded leaves, lower surface: 187A. Venation, upper surface: 183C underlain with 200A. Venation, lower surface: 187A. Petiole: Length: About 15 cm. Diameter: About 1.8 mm. Texture, upper and lower surfaces: Pubescent. Color, upper and lower surfaces: 187C underlain with 138D.

Flower description:

*Appearance/arrangement.*—Single campanulate flowers arranged on numerous erect panicles; about 66 to 140 flowers and flower buds per flowering stem. Flowers face outward to slightly upright. Flowering continuous. Flowers persistent. Flowers not fragrant.

*Time of flowering.*—Plants May through July in Scottdale, Pa.

*Inflorescence longevity.*—Individual inflorescences last about one week on the plant.

*Inflorescence size.*—Length: About 75 cm. Diameter: About 5 cm.

*Flower size.*—Diameter: About 4.2 mm. Depth (height): About 7 mm.

*Flower buds.*—Height: About 5.5 mm. Diameter: About 2.8 mm. Shape: Globular. Color, at stage of showing color: Close to 155D with glandular hairs, 57B.

*Sepals.*—Quantity/arrangement: Five sepals; radially symmetrical and fused at base. Calyx length: About 6 mm. Calyx diameter: About 4.2 mm. Shape: Elongate. Apex: Obtuse. Margin: Entire. Texture, upper and lower surfaces: Pubescent. Color, upper surface: Close to 155D. Color, lower surface: Close to 155D, towards the apex, 165B.

*Petals.*—Quantity/arrangement: Five minute petals; radially symmetrical. Length: About 4 mm. Width: About 1.2 mm. Shape: Spatulate. Apex: Acute. Margin: Entire with glandular hairs. Texture, upper and lower surfaces: Slightly pubescent. Color, upper and lower surfaces: Close to 155D.

*Flower bracts.*—Length: About 4.5 mm. Width: About 0.8 mm. Shape: Subulate. Apex: Acute. Margin: Serrate. Texture, upper and lower surfaces: Slightly pubescent. Color, upper and lower surfaces: 187C.

*Peduncle.*—Strength: Strong. Aspect: Mostly upright. Length: About 55 cm. Diameter: About 2.2 mm. Texture: Smooth. Color: 187C.

*Pedicels.*—Strength: Strong. Aspect: Erect to about 60° from vertical. Length: About 2 mm. Diameter: About 0.4 mm. Texture: Pubescent. Color: 187C.

*Reproductive organs.*—Androecium: Stamen number: Five per flower. Anther shape: Oval. Anther length: About 1 mm. Anther color: 23B. Amount of pollen: Moderate. Pollen color: 23B. Gynoecium: Pistil number: Two per flower. Pistil length: About 5.5 mm. Stigma shape: Round. Stigma color: 157C. Style length: About 4 mm. Style color: 157C. Ovary color: 157A.

*Seed.*—Size: About 0.3 mm by 0.6 mm. Color: Close to 202A.

Disease/pest resistance: Resistance to pathogens and pests common to *Heuchera* has not been observed on plants grown under commercial conditions.

Weather/temperature tolerance: Plants of the new *Heuchera* have been observed to have excellent garden performance. Plants of the new *Heuchera* have demonstrated good tolerance to rain, wind, night temperatures as low as −35° C., and day temperatures as high as 45° C.

It is claimed:

1. A new and distinct cultivar of *Heuchera* plant named 'Shenandoah Mountain', as illustrated and described.

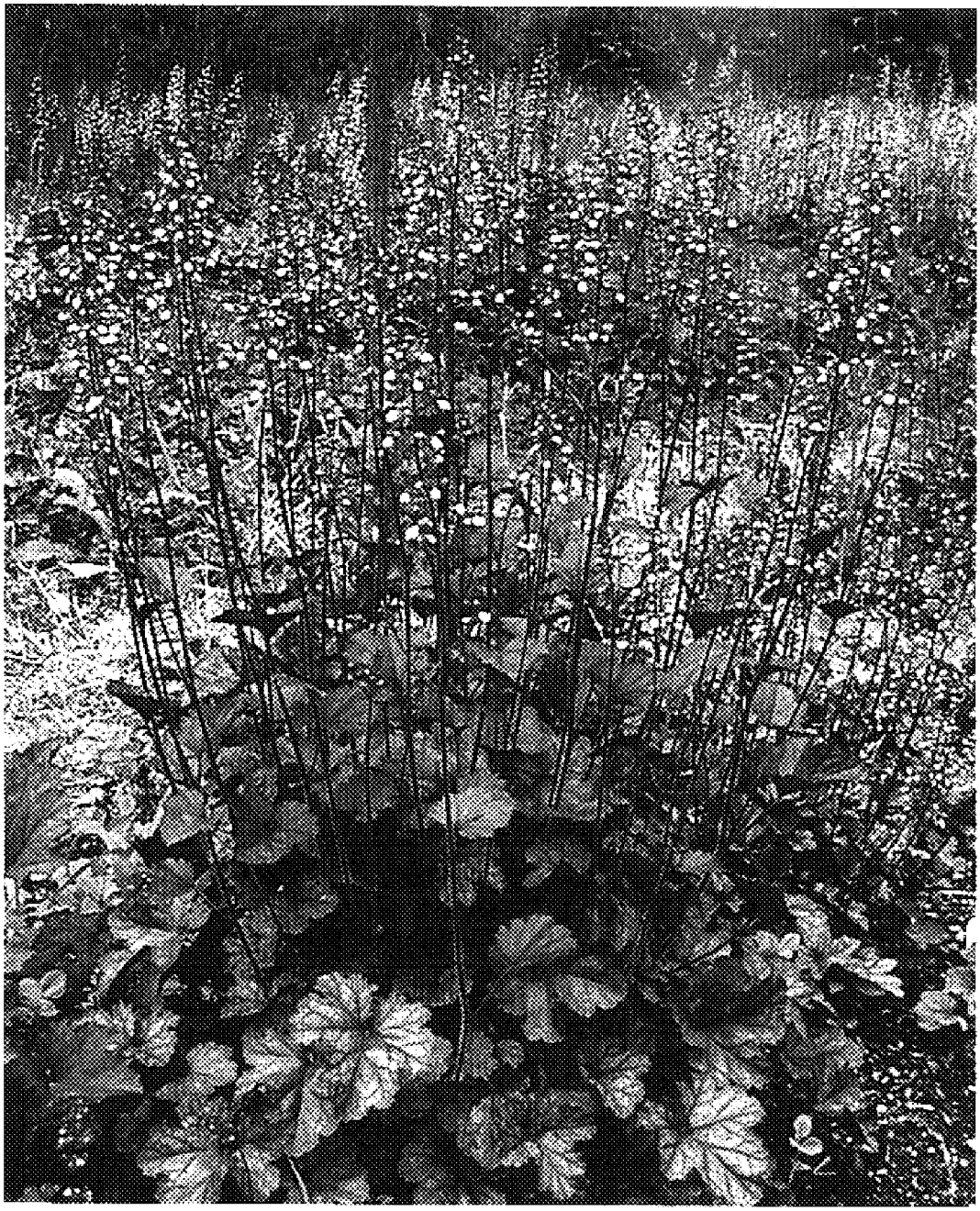

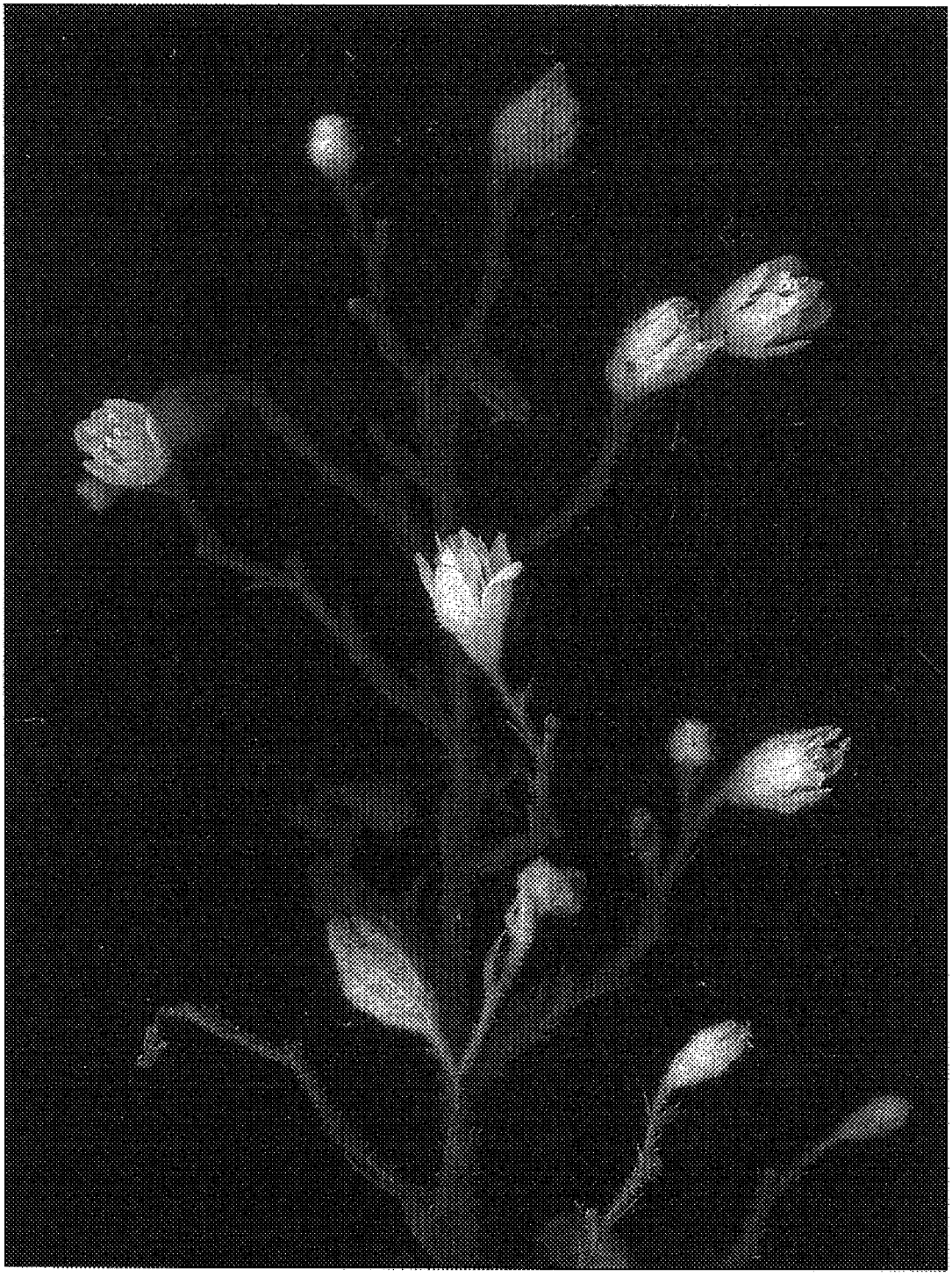

* * * * *